United States Patent [19]

Hardtmann et al.

[11] 4,412,952
[45] Nov. 1, 1983

[54] PROCESS FOR 3-HYDROXY BENZODIAZEPINONES

[75] Inventors: Goetz E. Hardtmann, Morristown; Oljan Repic, Hopatcong; Susi Vogt, Chatham, all of N.J.

[73] Assignee: Sandoz, Inc., E. Hanover, N.J.

[21] Appl. No.: 373,450

[22] Filed: Apr. 30, 1982

[51] Int. Cl.³ ........................................... C07D 243/26
[52] U.S. Cl. ............................................. 260/239.3 D
[58] Field of Search ................................. 260/239.3 D

[56] References Cited

U.S. PATENT DOCUMENTS 3,176,009 3/1965 Bell .............................. 260/239.3 D
3,296,249 1/1967 Bell .............................. 260/239.3 D
3,340,253 9/1967 Reeder et al. ............... 260/239.3 D

*Primary Examiner*—Robert T. Bond
*Attorney, Agent, or Firm*—Gerald D. Sharkin; Robert S. Honor

[57] ABSTRACT

Conversion of 3-acyloxy-benzodiazepin-2-ones into corresponding 3-hydroxy benzodiazepin-2-ones is carried out efficiently with potassium hydroxide or potassium alkoxide as catalyst in lower alkanol solvent at a pH of 11–11.5. The final products, which include temazepam, are useful as sleep inducers.

8 Claims, No Drawings

PROCESS FOR 3-HYDROXY BENZODIAZEPINONES

This invention concerns an improved process for the preparation of 3-hydroxy-benzodiazepin-2-ones. The process of the invention comprises conversion of 3-acyloxy-benzodiazepin-2-ones to the corresponding 3-hydroxy compounds by hydrolysis using a base containing potassium in lower alkanol solvent. The process may be depicted as follows:

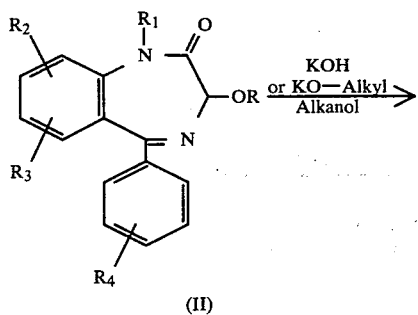

(II)

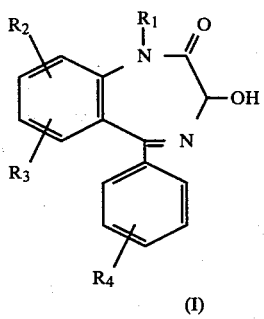

(I)

where

R represents an acyl moiety, such as $C_{2-8}$ alkanoyl, e.g. acetyl, propionyl or caproyl; phenoyl or phenoyl substituted with a loweralkyl, chloro or fluoro moiety, e.g., benzoyl or toluyl; phen $C_{2-5}$ loweralkanoyl such as phenacetyl or $\beta$-phenylpropionyl; or haloacyl such as chloroacetyl, chlorobenzoyl or bromobenzoyl, $R_1$ represents $C_{1-3}$ loweralkyl, such as methyl, ethyl or propyl, $R_2$ and $R_3$, independently, represent H, chloro, bromo, nitro, trifluoromethyl or methylsulfonyl, and $R_4$ represents H, chloro, fluoro, methoxy, methyl or trifluoromethyl.

The group "R" preferably represents a loweralkanoyl group having 2-4 carbons, such as acetyl or propionyl, especially acetyl. $R_1$ is preferably methyl, $R_2$ is preferably H, $R_3$ is preferably H, chloro, or trifluoromethyl, most preferably chloro, especially at the 7-position, and $R_4$ is preferably H. Where not otherwise indicated, halo preferably represents chloro or bromo and acyl is preferably $C_{2-8}$ alkanoyl, phenoyl, substituted phenoyl, or phen $C_{2-5}$ loweralkanoyl.

It is known in the art that compounds of general formula II may be hydrolized to compounds of general formula I. Thus, U.S. Pat. Nos. 3,176,009 and 3,296,249 disclose such hydrolysis by use of sodium hydroxide in ethanol. The former very generally discloses and claims such hydrolysis by use of dilute alkali metal hydroxide, although only sodium hydroxide is specifically disclosed. U.S. Pat. No. 3,340,253 discloses and claims that hydrolysis of this type may be performed under acidic conditions, such as by use of mineral acids or organic acids. Certain examples in this patent also disclose hydrolysis of a 3-acetoxy moiety of compounds similar to those with which this invention is concerned to a 3-hydroxy moiety by use of sodium hydroxide in ethanol or methanol as solvent.

It has now been discovered that particular reaction conditions significantly affect the quality and yield of products (I) obtainable from compounds (II). In particular, it has now been found that catalytic quantities of only very limited types of base (catalyst) are useful in the instant reaction to obtain the benefits now provided. The catalyst may be potassium hydroxide or 1-3 carbon potassium alkoxide, preferably potassium hydroxide or potassium methoxide, most preferably potassium hydroxide. Respecting the quantity of catalyst to be used, it has now been found that quantities of 1-1.7 percent of a mole, preferably 1.3-1.5 mole percent and most preferably 1.5 mole percent are useful in connection with this invention. The type and amount of catalyst used are critical aspects of this invention.

Most critical to this invention is the pH of the reaction medium. A pH of 11 to 11.5, preferably 11.2-11.4, most preferably pH 11.3, is essential in obtaining the desired result. Care should accordingly be exercised in maintaining the pH at these levels during the reaction. Respecting this reaction parameter, it should be understood that the pH described is the "apparent pH" noted in a non-aqueous medium and not corrected for temperature. In the laboratory work performed in connection with this invention, the pH was measured using a Horizon pH controller*.

*Model No. 5997 Horizon Ecology Co. Chicago, Ill.

It will be appreciated that the pH and the amount of catalyst utilized go hand in hand in providing the most favorable reaction conditions. Thus, an increase in the amount of catalyst utilized is not desirable as this will only increase the pH beyond its most preferred levels. And because even the amount of solvent utilized will have an effect on the pH, one should also be concerned with modification of the quantity of solvent in the reaction medium. It is emphasized that the most critical parameter in providing maximum yields and greatest purity of compound (I) in accordance with this invention is the pH of the reaction medium.

A third important aspect of this invention is the solvent medium in which the hydrolysis takes place. It has been found that lower alkanols having 1-3 carbon atoms, such as methanol, ethanol or propanol, most especially methanol, are solvents which would permit commercial use of the process of the invention without unnecessarily prolonged reaction times, or loss of control over quality of product.

The temperature of reaction is not critical, and about 0° C. to about 100° C. is an acceptable range, although 40°-80° C. is more convenient. About 65° C., the approximate reflux temperature of methanol, is especially convenient when methanol, the preferred solvent, is utilized.

The product of the reaction may be recovered by conventional techniques, e.g. precipitation, filtration, and recrystallization. It has been found that use of acetic acid and then water provides quite satisfactory results during recovery.

One of the preferred aspects of this invention concerns the preparation of temazepam, chemically identified as 7-chloro-1,3-dihydro-3-hydroxy-1-methyl-5-phenyl-2H-1,4-benzodiazepin-2-one, one of the compounds disclosed and claimed in the above-mentioned U.S. Pat. No. 3,296,249. This patent indicates that all the compounds of formula I hereof may be used as anticonvulsants and muscle relaxants, and that they exhibit psycholeptic, anti-anxiety and anti-tension effects. It has also been disclosed in the art that some of the compounds (I), especially temazepam, are active as sleep inducing agents. Temazepam is presently sold commercially as a sleep inducing agent for humans at doses of 15–30 mg before retiring.

In the following Examples, all temperatures are in degrees Centigrade and are uncorrected. All starting materials are obtainable using the processes described in the art for making such materials, or using analogous processes from known compounds.

EXAMPLE 1

To 400 ml of methanol is added 205 g. of O-acetyl temazepam (3-acetoxy-7-chloro-1,3-dihydro-1-methyl-5-phenyl 2H-1,4-benzodiazepin-2-one) and the resulting suspension is stirred and heated to reflux. Potassium hydroxide (0.505 g.) is dissolved in 422 ml methanol and added over a period of about one hour to the refluxing O-acetyl temazepam reaction mixture so that the aparent pH is maintained at 11.3±0.1. After the addition is complete, the resulting solution is clear and slightly yellow. The reaction mixture is stirred for an additional 15 minutes at reflux and 6 ml of acetic acid is then added until a pH of about 7.1 is achieved. Water (50 ml) at 65° C. is added to the solution which is then seeded with 0.2 g. of temazepam. The reaction mixture is cooled with stirring to 20° C. over two hours and 160 ml of water at 20° C. is then added over a 20 minute period. The mixture is stirred for an additional 15 minutes at 20° C. and is then gradually cooled to 0° C. over the course of one hour. Stirring is continued for an additional 30 minutes, the solids are filtered off, washed with 200 ml of water and dried at 50° C./20 mm Hg for 16 hours. The yield is 164.9 g. (91.7%) of temazepam (98.7% pure), m.p. 157.5°–160° C. This initial product is dissolved in 882 ml of abs. ethanol, by heating to reflux, and the hot solution is filtered through a preheated Buchner funnel. At 70° C., 412 ml of water and 0.2 g. of temazepam are added and the mixture is cooled to 20° C. over a three hour period. Water (494 ml) is added at 20° C. over 15 minutes and the mixture is stirred for an additional 15 minutes. The resulting suspension is cooled to 0°–5° C. over a one hour period, stirred for an additional 30 minutes, filtered and the crystals washed with 300 ml of water. The solids are dried at 50° C./20 mm Hg for 16 hours to obtain 149 g. (82.9%) of temazepam (m.p. 158°–160° C.) having a purity of about 99.8%.

When the above procedure is carried out and in place of 205 g. of O-acetyl temazepam there is used a corresponding quantity of 3-benzoyl-5-(o-chlorophenyl)-1,3-dihydro-1-methyl-8-trifluoromethyl-2H-1,4-benzodiazepine-2-one or 1,3-dihydro-1-methyl-7-nitro-3-phenacetyl-5-(p-trifluoromethylphenyl)-2H-1,4-benzodiazepine-2-one, there is obtained the corresponding 5-(o-chlorophenyl)-7-trifluoromethyl and 5-(p-trifluoromethylphenyl)-7-nitro analog of temazepam, respectively, in high yield and purity.

EXAMPLE 2

In comparing the procedure of this invention relative to the procedures described in the art for making temazepam, the results indicated in the table below were obtained.

|  | THIS INVENTION | Ex. 15 U.S. Pat. No. 3,296,249 | Ex. 32 U.S. Pat. No. 3,340,253 |
| --- | --- | --- | --- |
| 1 - crude product yield | 91.7% | 91.5% | 62.7% |
| 2 - analysis of crude product |  |  |  |
| a - temazepam | 98.7% | 36.3% | 91.7% |
| b - dione | 0 | 63.8% | 1.0% |
| c - oxazepam | 0.1% | 0.1% | 0.1% |
| 3 - final yield (from ethanol) | 82.9% | 46% | 53% |
| 4 - analysis of final product |  |  |  |
| a - temazepam | 99.8% | 68.2% | 96.1% |
| b - dione | 0.2% | 20.7% | 2% |
| c - oxazepam | <0.1% | 0 | 0 |
| d - mp. (°C.) | 158–160 | 119–122 | 153–156 |

What is claimed is:

1. A process for preparing a compound of the formula:

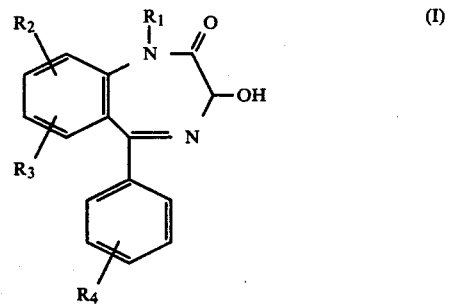

from a compound of the formula:

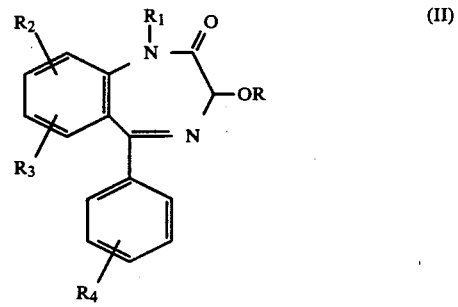

where

R represents $C_{2-8}$ alkanoyl, phenoyl, phenoyl substituted with a loweralkyl, fluoro or chloro moiety, phen $C_{2-5}$ loweralkanoyl, or haloacyl, $R_1$ represents $C_{1-3}$ loweralkyl, $R_2$ and $R_3$, independently, represent H, chloro, bromo, nitro, trifluoromethyl or methylsulfonyl, and $R_4$ represents H, chloro, fluoro, methoxy, methyl or trifluoromethyl, which comprises treating the latter with potassium hydroxide or 1–3 carbon potassium alkoxide as catalyst in a reaction medium comprising $C_{1-3}$ lower alkanol at a pH of 11 to 11.5.

2. A process according to claim 1 wherein R represents $C_{2-4}$ loweralkanoyl, $R_1$ represents methyl, $R_2$ and $R_4$ each represent H, and $R_3$ represents H, chloro or trifluoromethyl.

3. A process according to claim 2 wherein R represents acetyl, and $R_3$ represents chloro at the 7-position.

4. A process according to claim 1 wherein the catalyst is present to the extent of 1–1.7 mole percent.

5. A process according to claim 1 wherein the catalyst is present to the extent of 1.3–1.5 mole percent.

6. A process according to claim 1, 2, 3, 4 or 5 wherein the pH is maintained at 11.2–11.4.

7. A process according to claims 1, 2, 3, 4, 5 or 6 wherein the catalyst is potassium hydroxide.

8. A process according to claims 1, 2, 3, 4, 5, 6 or 7 wherein the lower alkanol is methanol.

* * * * *